(12) United States Patent
Zimbardi et al.

(10) Patent No.: US 11,260,021 B2
(45) Date of Patent: Mar. 1, 2022

(54) COSMETIC COMPLEX FOR BIOACTIVE HYDRATION, COSMETIC COMPOSITION, USE AND METHOD

(71) Applicant: Natura Cosméticos S/A, São Paulo (BR)

(72) Inventors: Daniela Zimbardi, São Paulo (BR); Selma Do Nascimento, São Paulo (BR); Cintia Rosa Ferrari, São Paulo (BR); Ana Paula Pedroso De Oliveira, São Paulo (BR); Andrea Arruda Costa, São Paulo (BR)

(73) Assignee: Natura Cosméticos S.A., São Paulo (BR)

( * ) Notice: Subject to any disclaimer, the term of this patent is extended or adjusted under 35 U.S.C. 154(b) by 33 days.

(21) Appl. No.: 16/635,750

(22) PCT Filed: Jul. 26, 2018

(86) PCT No.: PCT/BR2018/050258
§ 371 (c)(1),
(2) Date: Mar. 6, 2020

(87) PCT Pub. No.: WO2019/023774
PCT Pub. Date: Feb. 7, 2019

(65) Prior Publication Data
US 2021/0128451 A1    May 6, 2021

(30) Foreign Application Priority Data
Jul. 31, 2017   (BR) .......................... 1020170164250

(51) Int. Cl.
*A61K 8/9789*  (2017.01)
*A61K 8/34*    (2006.01)
*A61K 8/42*    (2006.01)
*A61K 8/60*    (2006.01)
*A61Q 19/00*   (2006.01)

(52) U.S. Cl.
CPC ............ *A61K 8/9789* (2017.08); *A61K 8/345* (2013.01); *A61K 8/42* (2013.01); *A61K 8/60* (2013.01); *A61Q 19/007* (2013.01); *A61K 2800/10* (2013.01); *A61K 2800/591* (2013.01)

(58) Field of Classification Search
None
See application file for complete search history.

(56) References Cited

U.S. PATENT DOCUMENTS

2016/0058689 A1* 3/2016 Wada ...................... A61K 8/37
424/61

FOREIGN PATENT DOCUMENTS

| CN | 106562910 A | 4/2017 |
|---|---|---|
| EP | 0180559 A2 | 5/1986 |
| WO | WO 2017/193186 A1 | 11/2017 |

OTHER PUBLICATIONS

EPO English translation of CN106562910 ([retrieved from on-line website: https://worldwide.espacenet.com/?locale=en_EP]) (Year: 2017).*

(Continued)

*Primary Examiner* — Kyung S Chang
(74) *Attorney, Agent, or Firm* — Alston & Bird LLP

(57) ABSTRACT

A novel cosmetic complex for bioactive hydration of the skin, particularly from the body and face, is provided. The cosmetic complex comprises vegetable oil, trehalose, and hydroxyethyl urea.

2 Claims, 1 Drawing Sheet

(56) References Cited

OTHER PUBLICATIONS

International Search Report and Written Opinion for Application No. PCT/BR2018/050258 dated Oct. 25, 2018, 17 pages.

* cited by examiner

COSMETIC COMPLEX FOR BIOACTIVE HYDRATION, COSMETIC COMPOSITION, USE AND METHOD

CROSS-REFERENCE TO RELATED APPLICATIONS

The present application is a national phase entry of PCT/BR2018/050258, filed on Jul. 26, 2018, which claims the benefit of priority of Brazilian patent application No. 1020170164250, filed Jul. 31, 2017, the entire contents of which are hereby incorporated by reference in their entirety for all purposes.

TECHNICAL FIELD

The present invention relates to a novel cosmetic complex for bioactive (or active or dynamic or biological) hydration of the skin, particularly from the body and face, comprising vegetal oil, trehalose as well as a cosmetic composition containing the same, the use thereof and a method for bioactive skin hydration.

BACKGROUND

The epidermis, the outermost layer of the skin, constantly renews itself and its last layer, which contacts the outer environment is designated the stratum corneum (EC). The EC comprises the final stage of epidermal cell differentiation and is specifically represented by dead and anucleated keratinized cells embedded in a lipid matrix that acts as a barrier that separates the external medium from the internal homeostasis.

The natural barrier formed by the EC mainly depends on its composition, which is represented by proteins (75-80%), lipids (5-15%) and other constituents (5-10%). The lipid composition of human EC may vary quantitatively between individuals and parts of the body, but mainly comprises ceramides, fatty acids, cholesterol, esters, triglycerides and phospholipids. When these components are not properly balanced the skin's ability to retain water is reduced and the skin becomes more prone to the influence of environmental factors causing an impaired barrier.

Water plays an important role in maintaining the EC barrier integrity. One of the main aspects relates to its ability to mediate the activity of many hydrolytic enzymes in the skin, including those responsible for the proper desquamation of corneocytes as well as those responsible for the formation of the natural moisturizing factor (NMF). As a proteolytic product of profilaggrins—a key molecule in the maintenance of the epidermal barrier—NMF is essentially composed of amino acids and derivatives thereof, PCA (pyrrolidone carboxylic acid), minerals, urea, sugars and peptides. This highly hygroscopic mixture aids in retaining EC hydration and, consequently, its function.

The epidermis is also responsible for skin regeneration. At every 28 days a cell migrates from the dermal-epidermal junction to the stratum corneum, then detaching itself as a dead cell in the process of desquamation. When the skin is dehydrated, this process of reconstitution and exchange is altered, making natural skin regeneration difficult. That is why skin hydration is so important for the skin.

When the stratum corneum surface is altered (for example, by burning, abrasions or rupture) or there is an excessive loss of lipids or natural moisturizers, the skin becomes dry, rough, without elasticity or flexibility. Sun, pollutants and relative air humidity are factors that also interfere with skin hydration.

Another key molecule for skin hydration is hyaluronic acid that is present in the dermis and in epidermal intercellular spaces. This molecule is able to bind up to a thousand times its weight with water molecules. In the dermis, together with other extracellular matrix molecules, it is responsible for retaining water and maintaining adequate tissue hydration.

In addition, membrane protein channels designated aquaporins are responsible for facilitating the transport of water and solutes, including glycerol and urea, across biological membranes. Such a transport of water takes place through an osmotic gradient.

Adult people should apply moisturizers on their skin at least once a day. These products generally include ingredients that typically act via two well-known mechanisms: occlusion and moisturizing.

Hydration by occlusion is promoted by ingredients that form a lipophilic film that prevents loss of water, hence increasing water retention in the horny layer.

Moisturizing hydration, in turn, is promoted by ingredients that retain water from the cosmetic composition, the atmosphere and the skin on the skin surface by means of a hydrophilic film formed on the horny layer, hence increasing water retention on the skin surface.

However, as a development of the aforementioned classic mechanisms other hydration mechanisms designated in the state of the art as active hydration have already been proposed. They generally refer to the use of ingredients having the ability to stimulate the skin to produce its own moisturizing substances, that is, molecules that are able to retain water in all layers of the skin.

Currently, the moisturizing properties of cosmetic skin preparations is demonstrated by non-invasive methods using instruments based on the skin electrical properties, such as conductance and capacitance, as well as spectroscopic techniques, such as NIR (near-infrared spectroscopy). However, there are issues associated with the reliability of measurements of the skin electrical properties (capacitance is the most used property to assess skin hydration) when it is treated with high concentrations of occlusive, nonpolar and non-hygroscopic ingredients. False negatives in water status measurements of the skin can be observed depending on the chemical composition of the formulation being studied. For this reason in some cases it is recommended to combine several instrumental techniques and even visual assessments with the aid of photographic scales to demonstrate the benefits of cosmetic skin preparations.

Dryness is one of the most present and chronic conditions of the skin, resulting in "stiffness" of the skin and damage to the skin in the form of cracks and fractures. Thus, assessment of the skin mechanical properties (using mechanical models) can be useful to provide an understanding on how damage to dry skin takes place (for example, cracking).

Thus, the state of the art still needs new moisturizing products capable of providing complete hydration of the skin, whether from the body or face, which act not only by the classic mechanisms of occlusion and moisturizing, but also by stimulating endogenous mechanisms to retain skin hydration as determined by more precise and reliable means.

SUMMARY

In one embodiment, a cosmetic complex for bioactive hydration is provided. The cosmetic complex may comprise at least one vegetable oil, trehalose, and hydroxyethyl urea.

In another embodiment, a method for bioactive hydration of the skin is provided. The method may comprise applying to the skin the complex described herein.

DETAILED DESCRIPTION

Figure 1:
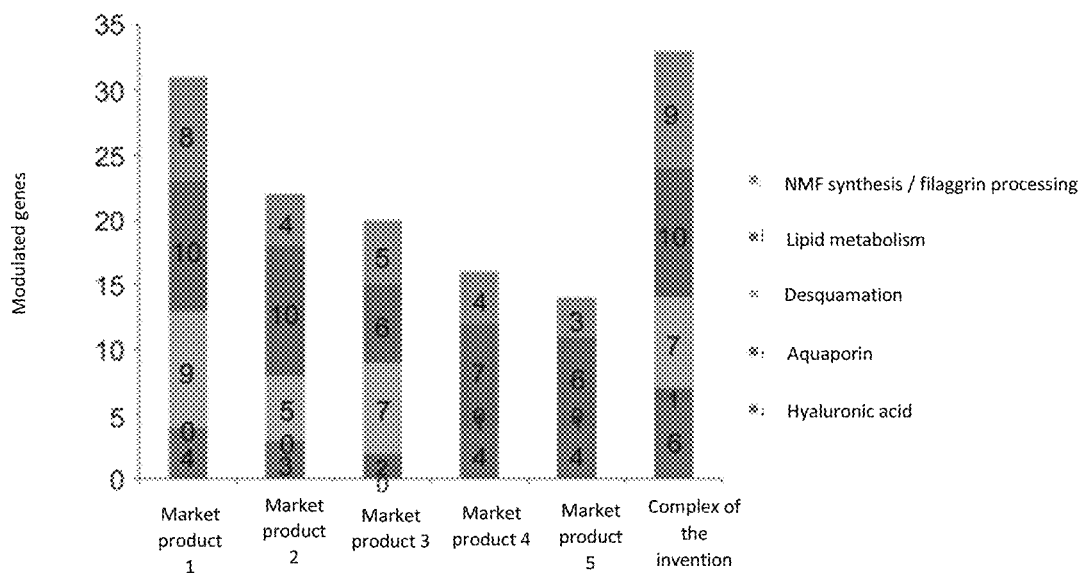
FIG. 1 shows gene expression results obtained from the complex according to the present invention as compared to other available products.

The present invention relates to a new cosmetic complex for bioactive hydration of the skin, particularly the body and face, which comprises:

(a) from about 0.05 to about 2% fevilea oil (*Fevillea trilobata*),
(b) from about 0.05 to about 4% trehalose
(c) from about 0.5 to about 4% hydroxyethylurea, and
(d) optionally glycerin.

The above percentages as well as those indicated in the examples below are based on the total weight of the final cosmetic composition in which the complex is contained.

According to the present invention, by "bioactive hydration", also designated herein as biological hydration or biodynamic hydration or active hydration, is meant the ability of a balanced combination of ingredients to stimulate endogenous mechanisms of the skin to promote a balance between the water and lipid contents for efficient hydration and nutrition.

Endogenous mechanisms that determine bioactive hydration according to the present invention are simultaneously:

(1) stimulation of molecules that retain water in the deeper layers of the skin (dermis) such as hyaluronic acid and other extracellular matrix components;

(2) stimulation of molecules that retain water on the skin surface such as natural moisturizing factors, also known as NMF (mineral salts);

(3) stimulation of the production and metabolism of molecules that retain lipids on the skin surface;

(4) stimulation of the adequate and balanced removal of dead cells from the skin surface (desquamation);

(5) stimulation of molecules that carry water and mineral salts to maintain the skin osmotic balance (such as, for example, aquaporins).

The effect on the five endogenous mechanisms above is assessed using techniques for the evaluation of gene and protein expression, which are highly accurate techniques and their results are independent of external factors, as is the case of the currently employed techniques.

Thus, the complex according to the present invention was surprisingly determined to be effective in stimulating the five endogenous mechanisms that characterize bioactive hydration. The balanced qualitative and quantitative combination of ingredients according to the present invention was able to stimulate the five endogenous skin mechanisms that promote a balanced water to lipid content for efficient hydration and nutrition, which characterize bioactive hydration.

In another embodiment, the present invention further comprehensively contemplates cosmetic compositions comprising the new bioactive hydration complex according to the present invention together with cosmetically acceptable excipients.

The cosmetically acceptable excipients according to the present invention are those known to the person skilled in the art for preparing cosmetic bases in various forms, for example, emulsions, creams, gels, serums, and others known to the person skilled in the art. For example, without being limited thereto, cosmetically acceptable excipients can be selected from those listed in the "International Cosmetic Ingredient Dictionary & Handbook", 16th Edition.

In another embodiment, the present invention further relates to the use of the complex to manufacture a cosmetic composition for bioactive hydration of the skin, particularly the body and face.

In yet another embodiment, the present invention contemplates a method for bioactive hydration of the skin which comprises applying on the skin, whether in need thereof or not, an effective amount of the complex or cosmetic composition according to the present invention. Thus, the method referred to herein can be either a preventive or cosmetic treatment.

The following examples, without any limitation, show the particular embodiments of the present invention and demonstrate the effectiveness of the complex according to the present invention in bioactive hydration.

EXAMPLES

Example 1. The Cosmetic Composition According to the Present Invention

The following table illustrates one embodiment of a cosmetic composition according to the present invention, which was produced by an emulsion preparation technique known to the person skilled in the art.

TABLE 1

Cosmetic composition according to the present invention

| Ingredient | % |
| --- | --- |
| Acrylates/$C_{10-30}$alkyl acrylate crospolymer | 0.2 |
| Water | 73.95 |
| Caprylic/capric triglyceride | 3.35 |
| Butirospermum parkii butter | 0.5 |
| Carbomer | 0.2 |
| Dimethicone | 5 |
| Disodium EDTA | 0.05 |
| Fragrance | 0.25 |
| Glycerin | 3 |
| Hydroxyethyl urea | 2 |
| Iodopropynyl butylcarbamate | 0.1 |
| Lecithin | 1.5 |
| Fevillea trilobata oil | 0.5 |
| Phenoxyethanol | 0.9 |
| Polymethylsilsesquioxane | 1 |
| Propylheptyl caprylate | 1 |
| Stearyl heptanoate | 3 |
| Tocopheryl acetate | 0.2 |
| Trehalose | 3 |
| Triethanolamine | 0.3 |

Example 2. Analysis of the Efficacy on Bioactive Hydration

To prepare the complex according to the present invention and demonstrate its efficacy, analysis of gene and protein expression was used to verify the modulation of genes involved in the stimulation of the endogenous skin mechanisms, which would promote the balance between the water and lipid contents for an efficient hydration and nutrition, that is, a bioactive hydration.

A large scale gene expression study was carried out followed by confirmation of protein expression to demonstrate the benefit.

The sample was tested on human skin explants obtained after plastic surgery (blepharoplasty) and the efficacy on the modulation of a total of 92 genes related to biological mechanisms relevant for skin hydration was evaluated, as well as some additional benefits such as integrity of the skin barrier, antioxidant properties, adhesion and cohesion between cells, cell renewal and anti-aging (elasticity, firmness, filling and dermal-epidermis cohesion).

In this experiment, skin fragments from 3 different donors were divided into two portions and immediately placed, in triplicate for each donor, in a culture medium. The explants were subjected to treatment with 2 mg/cm$^2$ of the sample applied topically, without any dilution, and maintained for 24 hours (portion 1) and 72 hours (portion 2) in a humid atmosphere at 37° C. in the presence of 5% $CO_2$. In addition, a control condition was performed by maintaining the explants, in triplicate for each donor, in culture medium only. A previous viability analysis was carried out to guarantee the integrity of the tissues throughout the study protocol.

Portion (1) was collected and subjected to total RNA extraction. cDNA was prepared from the RNA and the prepared cDNA (50 ng) was subjected to RT-PCR ("Real-Time Polymerase-Chain Reaction") to assess the expression of 96 genes. The gene expression profile and selection of differentially expressed genes were performed with the aid of Expression Suite Software v.1.0.3 (Life Technologies). ΔCt values for the reference and target genes were calculated by subtracting the values from the experimental groups. Subsequently, the ΔCt of the experimental group was subtracted from the control group (skin explant without treatment) to obtain ΔΔCt. Finally, the relative quantification of the target genes was determined by the equation: $RQ=2^{-\Delta\Delta Ct}$. Only genes having a threshold of 1.3, that is, 30% increase or decrease over the control, were selected. Statistical significance was assessed by the t-test combined with the Benjamini-Hochberg method (FDR—false discovery rate), wherein a p-value<0.05 was deemed significant.

For immunofluorescence detection, the samples were fixed in 4% paraformaldehyde (pH 7.4) for 24 hours and cryoprotected in a 30% sucrose solution for 48 hours. Then, 10 μm serial cuts were collected directly on slides coated with silane with the aid of a cryostat (Leica—CN1850). At the end of collection of the cuts, they were washed with 0.1 M PB and incubated overnight with antibodies related to the selected markers of interest. Then, the slides were analyzed using a Fluorescence Microscope (Leica—DM 1000) with the aid of the LAS Software (Leica Application Suite). The evaluated parameter was the fluorescence intensity emitted by staining with the specific antibody. Statistical analysis was made using analysis of variance (ANOVA). In all groups studied, those showing P values lower than 0.05 were considered statistically significant.

For Elisa detection commercially available kits (R&D Systems, USA) were used. The capture monoclonal antibody for the marker of interest was added to a 96-well plate, which was then incubated for 12 hours at room temperature. Samples were added and the plate was incubated for 2 hours at room temperature. The detection antibody for the marker of interest was then incubated for an additional 2 hours (RT). A streptavidin-peroxidase solution was added and incubated for 1 hour (RT). Finally, the substrate solution ($H_2O_2$ and TMB—tetramethylbenzidine) was added to the plate and a blue color developed within a period of 20 minutes. The staining reaction was stopped by adding 2N $H_2SO_4$ and the reading was performed on a 450 nm microplate reader. Protein levels were expressed in pg/ml or μg/ml and calculated from the reference values obtained with a standard curve built using known concentrations of the protein. Statistical analysis was made using analysis of variance (ANOVA). In all groups studied, those showing P values lower than 0.05 were considered statistically significant.

TABLE 2

Genes that had their expression evaluated in the study.

| Symbol | Gene |
| --- | --- |
| 18s Rna | RNA, 18S ribosomal [reference gene] |
| ACACA | Acetyl-CoA carboxylase 1 |
| ACACB | Acetyl-CoA carboxylase beta |
| AQP10 | Aquaporin-10 |
| AQP1 | Aquaporin-1 |
| AQP3 | Aquaporin-3 |
| AQP5 | Aquaporin-5 |
| ASAH1 | Acid ceramidase |
| BGN | Biglycan |
| CASP14 | Caspase-14 |
| CD44 | CD44 molecule (Indian blood group) |
| CDH1 | Cadherin-1 |
| CDSN | Corneodesmosin |
| CLDN1 | Claudin-1 |
| CLDN4 | Claudin-4 |
| CLDN7 | Claudin-7 |
| COL1A1 | Collagen, type I, alpha 1 |
| COL1A2 | Collagen, type I, alpha 2 |
| COL4A4 | Collagen, type IV, alpha 4 |
| COL7A1 | Collagen, type VII, alpha 1 |
| CRNN | Cornulin |
| CST6 | Cystatin 6 |
| CTSB | Cathepsin B |
| CTSD | Cathepsin D |
| CTSE | Cathepsin E |
| CTSL | Cathepsin L |
| CTSV | Cathepsin V |
| DCN | Decorin |
| DSC1 | Desmocollin 1 |
| DSC2 | Desmocollin 2 |
| DSG1 | Desmoglein 1 |
| DSG3 | Desmoglein 3 |
| DSG4 | Desmoglein-4 |
| DSP | Desmoplakin |
| ELN | Elastin |
| ELOVL3 | ELOVL fatty acid elongase 3 |
| EVPL | Envoplakin |
| FASN | Fatty acid synthase |
| FLG | Filaggrin |
| FMOD | Fibromodulin |
| GAPDH | Glyceraldehyde-3-phosphate dehydrogenase [reference gene] |
| GBA | Glucosylceramidase beta |
| GJA1 | Gap junction protein, alpha 1 |
| GJB2 | Gap junction protein, beta 2 |
| GPC3 | Glypican 3 |
| HAL | Histidine ammonia-lyase |
| GUSB | Glucuronidase, beta [reference gene] |
| HAS1 | Hyaluronan synthase 1 |
| HAS2 | Hyaluronan synthase 2 |
| HAS3 | Hyaluronan synthase 3 |
| HMGCR | 3-hydroxy-3-methylglutaryl-CoA reductase |
| HMGCS1 | 3-hydroxy-3-methylglutaryl-CoA synthase 1 |
| HMMR | Hyaluronan mediated motility receptor |
| HYAL1 | Hyaluronidase 1 |
| HYAL2 | Hyaluronidase 2 |
| HPRT | Hypoxanthine phosphoribosyltransferase [reference gene] |
| ITGA6 | Integrin alpha-6 |
| ITGB4 | Integrin beta-4 |
| IVL | Involucrin |
| KLF4 | Krueppel-like factor 4 |
| KLK5 | Kallikrein 5 |
| KLK7 | Kallikrein 7 |
| KRT1 | Keratin 1 |

TABLE 2-continued

Genes that had their expression evaluated in the study.

| Symbol | Gene |
|---|---|
| KRT10 | Keratin 10 |
| LAMA5 | Laminin subunit alpha-5 |
| LCE2B | Late cornified envelope protein 2B |
| LOR | Loricrin |
| LOX | Lysyl oxidase |
| LUM | Lumican |
| MATN2 | Matrilin 2 |
| MMP1 | Matrix metallopeptidase 1 |
| MMP12 | Matrix metallopeptidase 12 |
| MMP9 | Matrix metallopeptidase 9 |
| OCLN | Occludin |
| PADI1 | Peptidyl arginine deiminase, type 1 |
| PADI3 | Protein-arginine deiminase type 3 |
| PCNA | Proliferating cell nuclear antigen |
| PKP1 | Plakophilin 1 |
| PLEC | Plectin-1 |
| PPL | Periplakin |
| SDC1 | Syndecan 1 |
| SMPD1 | Sphingomyelin phosphodiesterase/Acid sphingomyelinase |
| SOD2 | Superoxide dismutase 2, mitochondrial |
| SPINK5 | Serine peptidase inhibitor, Kazal type 5 |
| SPTLC2 | Serine palmitoyltransferase, long chain base subunit 2 |
| SREBF2 | Sterol regulatory element-binding protein 2 |
| ST14 | Suppression of tumorigenicity protein 14 |
| TGM1 | Transglutaminase-1 |
| TGM3 | Transglutaminase-3 |
| TGM5 | Transglutaminase-5 |
| TIMP1 | TIMP metallopeptidase inhibitor 1 |
| TIMP2 | TIMP metallopeptidase inhibitor 2 |
| TJP1 | Tight junction protein 1 |
| UGCG | Ceramide glucosyltransferase |
| VCAN | Versican |
| VCL | Vinculin |

Figure 2:
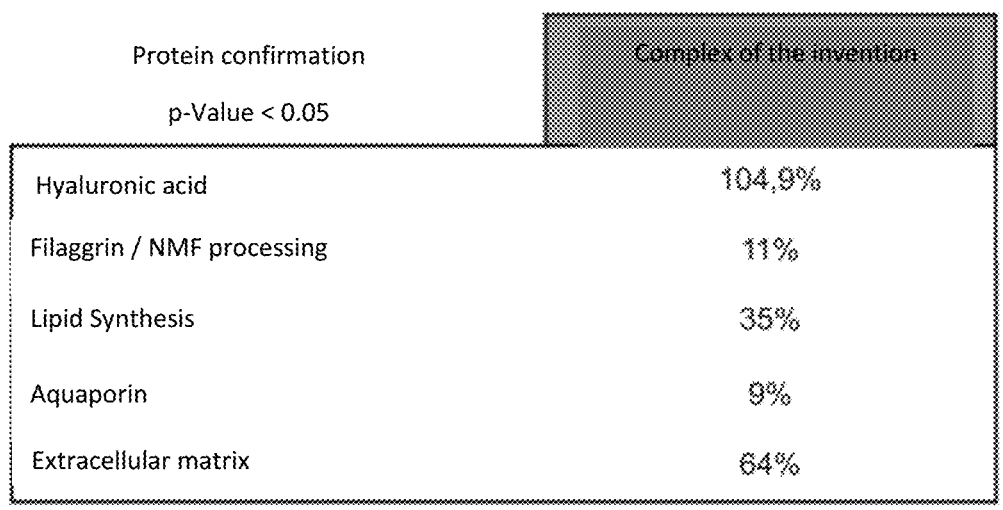
FIG. 2 shows protein expression results of the complex for some selected markers.

FIGS. 1 and 2 show, respectively, the gene expression results obtained from the complex according to the present invention as compared to their ingredients alone and compared with other products available in the market.

As can be seen, the complex according to the present invention was the only one capable of acting on the five endogenous mechanisms that determine the occurrence of bioactive hydration, both in comparison to their isolated components and to well-established moisturizing products available in the market.

Example 2. Stability Study

Accelerated stability studies under conditions of dark, 5° C. and 40° C. have shown that the formulations did not undergo significant changes in up to 90 days of use, considering stable cosmetic compositions under the studied conditions.

The skilled person can readily evaluate, based on the teachings provided in the text and in the examples presented herein, the advantages of the invention and to propose equivalent variations and alternative embodiments, without departing from the scope of the invention, as defined in the appended claims.

The invention claimed is:

1. A cosmetic complex for bioactive hydration comprising at least one vegetable oil, trehalose, and hydroxyethyl urea, and wherein the vegetable oil comprises fevilea oil, wherein the complex comprises:
   (a) from about 0.05 to about 2% fevilea oil,
   (b) from about 0.05 to about 4% trehalose, and
   (c) from about 0.5 to about 4% hydroxyethyl urea.

2. The complex according to claim 1, further comprising glycerin.

* * * * *